(12) United States Patent
Ursin et al.

(10) Patent No.: US 7,163,960 B2
(45) Date of Patent: Jan. 16, 2007

(54) TREATMENT AND PREVENTION OF INFLAMMATORY DISORDERS

(75) Inventors: Virginia Ursin, Davis, CA (US); Michael J. James, Dulwich (AU)

(73) Assignees: Monsanto Technology L.L.C., St. Louis, MO (US); Royal Adelaide Hospital, Adelaide (AU)

( * ) Notice: Subject to any disclaimer, the term of this patent is extended or adjusted under 35 U.S.C. 154(b) by 168 days.

(21) Appl. No.: 10/384,369

(22) Filed: Mar. 7, 2003

(65) Prior Publication Data

US 2004/0039058 A1 Feb. 26, 2004

Related U.S. Application Data

(60) Provisional application No. 60/365,872, filed on Mar. 8, 2002.

(51) Int. Cl.
*A61K 31/20* (2006.01)
(52) U.S. Cl. .................................... 514/560
(58) Field of Classification Search ................ 514/560
See application file for complete search history.

(56) References Cited

U.S. PATENT DOCUMENTS

| | | | |
|---|---|---|---|
| 4,681,896 A * | 7/1987 | Horrobin ................. | 514/552 |
| 5,130,449 A | 7/1992 | Lagarde et al. ........... | 554/186 |
| 5,158,975 A | 10/1992 | Guichardant et al. ...... | 514/560 |
| 5,178,873 A * | 1/1993 | Horrobin et al. .......... | 424/422 |
| 5,434,183 A * | 7/1995 | Larsson-Backstrom ..... | 514/549 |
| 5,683,698 A * | 11/1997 | Chavali et al. ........... | 424/756 |
| 6,326,355 B1 | 12/2001 | Abbruzzese et al. ....... | 514/21 |
| 6,340,485 B1 | 1/2002 | Coupland et al. ......... | 424/776 |

FOREIGN PATENT DOCUMENTS

| | | |
|---|---|---|
| DE | 197 57 414 | 1/1999 |
| EP | 0 347 056 | 12/1989 |
| EP | 0 460 848 | 12/1991 |
| WO | WO 99/42101 | 8/1999 |
| WO | WO 02/092779 | 11/2002 |

OTHER PUBLICATIONS

Harrison's Principles of Internal Medicine, Isselbacher et al. (eds.), vols. 1-2, 13th edition, published 1994 by McGraw-Hill, Inc. pp. 1116, 1167, 1403, 1643, 1648 and 2379.*
Ablumunits et al., "Islet T cells secreting IFN-γ in NOD mouse diabetes: arrest by p277 peptide treatment," *J. Autoimmun.*, 11:73-81, 1998.
Beisel, "Herman award lecture, 1995: infection-induced malnutrition—from cholera to cytokines," *Am. J. Clin. Nutr.*, 62:813-819, 1995.
Bruserud, "Effects of endogenous interleukin 1 on blast cells derived from acute myelogenous leukemia patients," *Leukemia Res.*, 20:65-73, 1996.
Cerami et al., "Weight loss associated with an endotoxin-induced mediator from peritoneal macrophages: the role of cachectin (tumor necrosis factor)," *Immunol. Lett.*, 11:173-177, 1985.
Cominelli and Pizarro, "Interleukin-1 and interleukin-1 receptor antagonist in inflammatory bowel disease," *Ailment Pharmacol. Ther.*, 10:49-53, 1996.
Fong et al., "Antibodies to cachectin/tumor necrosis factor reduce interleukin 1β and interleukin 6 appearance during lethal bacteremia," *J. Exp. Med.*, 170:1627-1633, 1989.
Fong et al., "Cachectin/TNF or IL-1α induces cachexia with redistribution of body proteins," *Am. J. Physiol.*, 256:R659-R665, 1989.
Gruol et al., "Physiological and pathological roles of interleukin-6 in the central nervous system," *Molecular Neurobiology*, 15:307-339, 1997.
Hotamisligil and Spiegelman, "Tumor necrosis factor alpha: a key component of the obesity-diabetes link," *Diabetes*, 43(11):1271-1278, 1994.
Howells, "Cytokine networks in destructive periodontal disease," *Oral Dis.*, 1:266-270, 1995.
James et al., "Metabolism of stearidonic acid in human subjects: comparison with the metabolism of other n-3 fatty acids," *Am. J. Clin. Nutr.*, 77:1140-1145, 2003.
Janeway et al., In: *Immunobiology—The Immune System in Health and Disease*, 4th Edition, Elsevier Scinece Ltd/ Garland Publsihing, 1999.
Mantzioris et al., "Biochemical effects of a diet containing foods enriched with n-3 fatty acids," *Am. J. Clin. Nutr.*, 72:42-48, 2000.
Mantzioris et al., "Dietary substitution with an α-linolenic acid-rich vegetable oil increases eicosapentoaenoic acid concentrations in tissues," *Am. J. Clin. Nutr.*, 59:1304-1309, 1994.
McCarthy et al., "Suppression of food intake during infection: is interleukin-1 involved?" *Am. J. Clin. Nutr.*, 42:1179-1182, 1985.
Moldawer et al., "Regulation of food intake and hepatic protein synthesis by recombinant-derived cytokines," *Am. J. Physiol.*, 254:G450-G456, 1988.
Moller, "Potential role of TNF-alpha in the pathogenesis of insulin resistance and type 2 diabetes," *Trends Endocrinol Metab*, 11(6):212-217, 2000.
Rankin et al., "The therapeutic effects of an engineered human anti-tumour necrosis factor alpha antibody (CDP571) in rheumatoid arthritis," *British J. Rheum.*, 34:334-342, 1995.
Ridker et al., "C-reactive protein and other markers of inflammation in the prediction of cardiovascular disease in women," *New England Journal of Medicine*, 342(12):836-843, 2000.
Simopoulos, "ω-3 fatty acids in the prevention-management of cardiovascular disease," *Can. J. Physiol. Pharmacol.*, 75:234-239, 1997.

(Continued)

*Primary Examiner*—Raymond J. Henley, III
(74) *Attorney, Agent, or Firm*—Fulbright & Jaworski L.L.P.

(57) ABSTRACT

The invention relates to methods of treating and preventing disorders associated with elevated TNF-α and/or IL-1β by administering therapeutic amounts of stearidonic acid. Further provided are methods for down-regulating TNF-α and/or IL-1β and assays for determining the presence, absence, or quantity of TNF-α and/or IL-1β in a subject in conjunction with a regimen of stearidonic acid administration.

10 Claims, 1 Drawing Sheet

OTHER PUBLICATIONS

Stack et al., "Randomised controlled trial of CDP571 antibody to tumour necrosis factor-α in Crohn's disease," *Lancet*, 349:521-524, 1997.

Caughey et al., "The effect on human tumor necrosis factor α and interleukin 1β production of diets enriched in n-3 fatty acides from vegetable oil or fish oil 1-3," *Am J. Clin. Nutr.*, 63:116-122, 1996.

Heesen et al., "IL-1ra serum levels in disease stages of ms—a marker for progression," *Acta Neurol Scand*, 101:95-97, 2000.

* cited by examiner

TREATMENT AND PREVENTION OF INFLAMMATORY DISORDERS

This application claims the priority of U.S. Provisional Patent Application Ser. No. 60/365,872, filed Mar. 8, 2002.

BACKGROUND OF THE INVENTION

1. Field of the Invention

The present invention relates generally to methods for treating and prevention of disorders associated with increased TNF-α and IL-1β by administering therapeutically effective amounts of stearidonic acid.

2. Description of Related Art

Inflammation is the body's response to injuries caused by mechanical damage, infection, or antigenic stimulation, and is therefore a beneficial process for health and survival. However, inflammation can also be induced by inappropriate stimuli such as autoantigen stimulation, which frequently leads to development of autoimmune diseases. Inflammation also can significantly contribute to the pathophysiology of such diseases.

The characteristics of inflammation include heat, redness, pain, and swelling, all of which are at least partly attributable to the effects of cytokines on the local blood vessels. Cytokines are non-antibody proteins secreted by inflammatory leukocytes and some non-leukocytic cells, that act as intercellular mediators. They differ from classical hormones in that they are produced by a-number of tissue or cell types rather than by specialized glands. They generally act locally in a paracrine or autocrine rather than endocrine manner.

Proinflammatory cytokines include tumor necrosis factor, such as TNF-α; interleukins, such as IL-1β, IFN-γ, IL-8, IL-6; including granulyte macrophage colony stimulating factor (GM-CSF); all playing a major role in initiating inflammatory responses and keeping the inflammation process going. Such cytokines, mediators of inflammation, lead to changes in vascular diameter, blood flow, and expression of adhesion molecules on the endothelial cells of local blood vessels, thereby leading to extravasation of immune cells to the sites of inflammation.

For instance, IL-8 acts as a chemoattractant for neutrophils, thus allowing for more efficient extravasation of these cells to the sites of injury. Antibodies blocking against IL-8 have demonstrated the role for IL-8 in the neutrophil associated tissue injury in acute inflammation (Harada et al., *Molecular Medicine Today*, 2:482, 1996). IL-6 is also a mediator of inflammation, especially in the central nervous system. Elevated levels of IL-6 are found in disorders such as systemic lupus erythematosus, multiple sclerosis, and viral and bacterial meningitis (Gruol et al., *Molecular Neurobiology*, 15:307, 1997). GM-CSF is a proinflammatory cytokine that is involved in bronchial asthma (Lee, J. R., *Coll Physicians Lond*, 32:56, 1998). IFN-γ has been associated with increased collagen deposition, which is observed in graft-versus-host disease (Parkman, *Curr. Opin. Hematol.*, 5:22, 1988). The development of insulin-dependent diabetes (Type I) has been correlated with the accumulation of T-cell produced IFN-γ in pancreatic islets (Ablumunits, et al., *J. Autoimmun.*, 11:73, 1998).

TNF-α and IL-1 are synthesized by monocytes and other cells in response to injury, as well as to infectious, inflammatory, or immunologic challenges. These cytokines are involved in a multitude of inflammatory disorders and can cause significant damage through their exerted actions. Among the biological actions of IL-1 are: activation of vascular endothelium, activation of lymphocytes, local tissue destruction, and the promotion of increased access of effector cells to the sites of inflammation. Some of the major effects of TNF-α include increased fluid drainage to lymph nodes and increased vascular permeability, thus leading to increased entry of IgG antibodies, complement, and cells to injured tissues (Charles A. Janeway, Jr., Paul Travers, Mark Walport, and J. Donald Capra, *Immunobiology*, Fourth Edition, Elsevier Science Ltd/Garland Publishing, 1999). IL-1 and TNF-α often act synergistically, for example, on vascular endothelium and on the synthesis of metabolites of arachidonic acid.

The involvement of TNF-α in a number of diseases has been clinically demonstrated by administering anti-TNF-α monoclonal antibody to patients afflicted with rheumatoid arthritis, Chron's disease, and ulcerative colitis (Rankin E. C. C., et al., *British J. Rheum*, 35:334–342, 1997, and Stack, W. A., et al., *Lancet* 349:521–524, 1997). Elevated levels of IL-1 have been demonstrated in patients with inflammatory bowel disease (IBD). Insufficient production of endogenous IL-1ra may contribute to pathogenesis of IBD (Cominelli, et al., 1996, *Ailment Pharmacol. Ther.*, 10, 49, 1996). IL-1 and TNF-α are both involved in periodontal disease (Howells, Oral Dis., 1, 266, 1995). In addition, IL-1, TNF-α, and GM-CSF have been shown to stimulate proliferation of acute myelogenous leukemia blasts (Bruserud, *Leukemia Res.*, 20, 65, 1996). TNF-α and IL-1, together with IL-6 and IL-8, initiate acute phase response observed in fever, malaise, myalgia, etc. (Beisel, *Am. J. Clin. Nutr.*, 62:813, 1995), and are thus commonly observed following trauma or pathogen invasion.

The serious problems associated with septic shock are mostly due to the actions of TNF-α. In septic shock, vasodilation, increased vascular permeability, and blood clotting are initiated by TNF-α and often lead to failure of organs such as kidneys, liver, heart, and lungs. Cachexia, which is a common symptom of prolonged infection or advanced malignancy, results from chronic exposure to TNF-α or IL-6. In addition, animal studies performed in mice and rats have further shown that administration of TNF-α or IL-1 leads to anorexia, weight loss, and depletion of body lipids and proteins within 7 to 10 days (Cerami et al, *Immunol Lett.*, 11:173, 1985; Fong et al., *J. Exp. Med.*, 170:1627, 1989; Moldawer et al., *Am. J. Physiol*, 254: G450–G456,1988; Fong et al., *Am. J. Physiol*, 256: R659–R665, 1989; McCarthy et al., Am. J. Clin. Nutr., 42:1179–1182, 1982).

The role of TNF-α and/or IL-1 has been demonstrated in the pathophysiology of many inflammatory disorders. In recent years, new evidence related to the role of inflammation in cardiovascular disease, and particularly in atherosclerosis has started to emerge. This is highly relevant given that cardiovascular disease is the number one cause of mortality in the world. Atherosclerosis is characterized by deposition of plaques that contain cholesterol, lipoid material, and lipophages in large and medium-sized arteries. Formation of plaques often leads to inadequate coronary blood flow to the ventricular myocardium, leading to conditions such as ischemia and pain (angina pectoris) and death of cardiac muscle (myocardial infarction). One such marker of systemic inflammation that is produced in the liver is high-sensitivity C-reactive protein (hsCRP). HsCRP has been shown to be the strongest univariate predictor of the risk of cardiovascular events (NEJM Vol. 342 no. 12:836).

It has been known that oxidative modification of low-density cholesterol plays a role in the deposition of plaques in the arteries. However, according to Paul Ridker, a Harvard cardiologist, it is highly likely that inflammation plays an important part in atherosclerosis by destabilizing plaques, thereby leading to their mobilization through the blood stream. In support of this theory is the fact that aspirin, which has blood thinning and anti-inflammatory properties, decreases the chances of a heart attack even though aspirin has no effect on cholesterol or lipid profile.

It is also known that long chain omega-3 fatty acids such as eicosapentaenoic acid (EPA, 22:5, n-3) and docosahexaenoic acid (DHA, 22:6, n-3), which are found in fish and fish oil, are responsible for many of the health benefits attributed to polyunsaturated fatty acids, including inhibition of inflammation.

Omega-3 (n-3) fatty acids are polyunsaturated fatty acids in which a double bond is located between the third and fourth carbon atom from the methyl end of the fatty acid chain. They include, but are not limited to, α-linolenic acid (ALA, 18:3, n-3), stearidonic acid (SDA,18:4, n-3), eicosapentaenoic acid (EPA, supra), docosapentaenoic acid (22:5, n-3) and docosahexaenoic acid (DHA, supra) and the like. Relatedly, omega-6 fatty acids ("n-6") have a first double bond at the sixth carbon from the methyl end of the chain; and include, but are not limited to, linoleic acid (LA, 18:2), γ-linolenic acid (GLA, 18:3, n-6), arachidonic acid (AA, 20:4, n-6), and the like. Arachidonic acid is the principal precursor for the synthesis of eicosanoids, which include leukotrienes, prostaglandins, and thromboxanes, and which also play a role in the inflammation process. Administration of an omega-3 fatty acid, such as SDA, has been shown to inhibit biosynthesis of leukotrienes (U.S. Pat. No. 5,158, 975).

Omega-3 fatty acids are scarce in a normal Western diet but make up a significant part of fat intake in diets rich in cold-water fish and seal meat. Epidemiological studies-in populations of coastal Eskimo, Japanese, and Dutch populations have shown that a high intake of omega-3 fatty acids correlates with a low incidence of cardiovascular and inflammatory diseases, such as asthma and Type I diabetes mellitus. Thus, a number of studies have demonstrated the health benefits of omega-3 fatty acids. However, it previously was unknown that SDA can be administered to down-regulate TNF-α and IL-1β. Furthermore, as discussed below, the current use of natural and synthetic sources of SDA pose a number of problems.

At present, existing treatments for inflammatory disorders frequently are accompanied by a multitude of issues. For example, since many of the drugs given to treat autoimmune diseases are based on inhibiting a patient's immune system, they also compromise a patient's ability to fight infections. More importantly, these drugs may be accompanied by serious, and sometimes life-threatening side-effects. For example, while corticosteroids (also known as glucocorticoids) such as prednisone and methylprednisone are effective at controlling rheumatoid arthritis, Systemic Lupus Erythematosus (SLE), graft vs. host disease, and a number of other autoimmune diseases, their side-effects include osteoporosis, fluid retention, weight gain, onset or worsening of diabetes, cataracts, and hypertension. Another group of drugs, broadly categorized as immuno-suppressants such as methotrexate, azathioprine, cyclosporine, and leflunomide are also effective at regulating the immune system. However, their side-effects include potential liver problems and low white blood cell count (methotrexate), blood abnormalities (azathioprine), hypertension, loss of kidney function, tremors (cyclosporine), diarrhea, skin rashes, and liver problems (leflunomide). Recent development of anti-TNF-α monoclonal antibodies for treatment of rheumatoid arthritis has proven to be a successful treatment for alleviating the symptoms of the disease, however the administration is via injection, and can be painful and difficult to use.

Accordingly, omega-3 fatty acids could successfully be used to treat a number of inflammatory disorders. However, provision of EPA and DHA, which show great potential for such treatments, can be difficult to obtain or otherwise problematic.

There are several disadvantages associated with commercial production of polyunsaturated fatty acids (PUFAs) from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFAs. Natural sources also are subject to uncontrollable fluctuations in availability. Fish stocks may undergo natural variation or may be depleted by overfishing. Fish oils, which contain high levels of EPA and DHA generally have unpleasant tastes and odors. These undesirable attributes may be impossible to economically separate from the desired product, and can render such products unacceptable as food supplements. In addition, animal oils, and particularly fish oils, can accumulate environmental pollutants. Crops which do produce desirable PUFAs, such as borage, have not been adapted to commercial growth and may not perform well in monoculture. Use of microorganisms for production of PUFAs can also present significant problems. For instance, microorganisms such as Porphyridium and Mortierella are difficult to cultivate on a commercial scale. In addition, large scale fermentation of organisms such as Mortierella is expensive.

Dietary supplements and pharmaceutical formulations containing PUFAs can retain the disadvantages of the PUFAs source. Supplements such as fish oil capsules can contain low levels of the particular desired component and thus require large dosages. High dosages result in ingestion of high levels of undesired components, including contaminants. Unpleasant tastes and odors of the supplements can make such regimens undesirable, and may inhibit compliance by the patient. Care must be taken in providing fatty acid supplements, as over-addition may result in suppression of endogenous biosynthetic pathways and lead to competition with other necessary fatty acids in various lipid fractions in vivo, leading to undesirable results. For example, Eskimos having a diet high in ω-3 fatty acids have an increased tendency to bleed (U.S. Pat. No. 4,874,603; Saynor and Varell, *Medical Science* 8:379 (1980)).

Thus, it is desirable to provide novel and culturally acceptable ways in which to utilize PUFAs to regulate proinflammatory cytokines. The below described invention fulfills this need.

SUMMARY OF THE INVENTION

Applicants have determined that relatively small amounts of SDA are therapeutically effective modulators of proinflammatory cytokines such as TNF-α and IL-1β. Because administration of such small amounts are therapeutic, daily ingestion of therapeutically effective amounts of SDA can be accomplished efficiently and efficaciously through ingestion of SDA-enhanced foods or other edible compositions. Briefly, therefore, one aspect of the present invention is directed to methods for down-regulating TNF-α in a mammal exhibiting elevated concentrations of TNF-α, wherein the methods comprise administering therapeutically effective amounts of stearidonic acid to the mammal for a time period effective to down-regulate TNF-α. In addition, the present invention provides methods for down-regulating IL-1β in a mammal exhibiting elevated concentrations of IL-1β, wherein the methods comprise administering therapeutically effective amounts of stearidonic acid to the mammal for a time period effective to down-regulate IL-1β.

In another aspect, the present invention is directed to methods for down-regulating TNF-α and/or IL-1β in a mammal exhibiting elevated concentrations of TNF-α and/or IL-1β, wherein the methods comprise administering therapeutically effective amounts of stearidonic acid to the mammal for a time period effective to down-regulate TNF-α and/or IL-1β. In one embodiment of the invention, elevated concentrations of TNF-α and/or IL-1β are present in a mammal due to an inflammatory disorder. The disorder may, in one embodiment, comprise cardiovascular disease, rheumatoid arthritis, multiple sclerosis, Crohn's disease, inflammatory bowel disease, systemic lupus erythematosis, polymyositis, septic shock, graft vs. host disease, asthma, rhinitis, psoriasis, cachexia associated with cancer, and eczema. In another embodiment of the invention, the mammal is a human.

In a further embodiment of the invention, a therapeutically effective amount of stearidonic acid administered as described herein is from about 0.1 g/day to about 10 g/day. In certain embodiments, the therapeutic amounts are from about 0.25 g/day to about 8 g/day, from about 0.5 g/day to about 5 g/day or about 1.5 g/day.

In yet another aspect of the invention, disorders associated with elevated TNF-α and/or IL-1β can be treated by the methods described herein, including, but not limited to: cardiovascular disease, rheumatoid arthritis, multiple sclerosis, Crohn's disease, inflammatory bowel disease, systemic lupus erythematosis, polymyositis, septic shock, graft vs. host disease, asthma, rhinitis, psoriasis, cachexia associated with cancer, and eczema. Preferably, the inflammatory disorders comprise cardiovascular disease and rheumatoid arthritis, and more preferably, the cardiovascular disease is atherosclerosis.

In another embodiment of the invention, the therapeutically effective amounts of stearidonic acid comprise amounts that are effective at altering the blood concentration of TNF-α and IL-1β.

In yet another aspect, the present invention involves methods of preventing an inflammatory disorder wherein the inflammatory disorder is characterized by elevated levels of TNF-α and/or IL-1β in a mammal in need of such treatment comprising administering to the mammal therapeutically effective amounts of stearidonic acid for a time period effective to prevent the inflammatory disorder.

The present invention also provides methods for altering eicosapentaenoic acid level in a human, the methods comprising administering therapeutically effective amounts of stearidonic acid. In another embodiment, the present invention involves an assay comprising an analysis of blood and/or tissue from a subject to determine the presence, absence or quantity of TNF-α and/or IL-1β, wherein the analysis is performed before, during or after administration of stearidonic acid to the subject.

In still another embodiment of the present invention, an assay is used to determine a therapeutically effective amount of stearidonic acid to administer to a subject.

In yet another aspect, the invention provides a method of down-regulating C-reactive protein in a mammal having elevated concentrations of C-reactive protein, comprising identifying a mammal having elevated concentrations of C-reactive protein and administering to the mammal a therapeutically effective amount of stearidonic acid (18:4, n-3) over a time period effective to down-regulate C-reactive protein, whereby C-reactive protein is down-regulated. In certain embodiments of the invention, the subject may further comprise elevated TNF-α and/or IL-1β and these levels may be down-regulated by administering the SDA.

In still yet another aspect, the invention provides a method of preventing an inflammatory disorder characterized by elevated levels of C-reactive protein in a mammal in need of such treatment comprising identifying a mammal at risk for an inflammatory disorder characterized by elevated levels of C-reactive protein and administering to the mammal an amount of stearidonic acid (18:4, n-3) over a time period effective to prevent the an inflammatory disorder characterized by elevated levels of C-reactive protein. In certain embodiments of the invention, the inflammatory disorder may be further characterized by elevated TNF-α and/or IL-1β and these levels may be down-regulated by administering the SDA.

In still yet another aspect, the invention provides a method reducing or eliminating the deleterious effects of a condition associated with elevated C-reactive protein comprising screening the subject to identify an elevated presence of C-reactive protein and administering to the subject an effective amount of stearidonic acid (18:4, n-3) over a time period sufficient to down-regulate C-reactive protein, wherein the C-reactive protein is decreased and wherein the deleterious effects of the condition are reduced or eliminated. In certain embodiments of the invention, the condition may be further characterized by elevated TNF-α and/or IL-1β and these levels may be down-regulated by administering the SDA, wherein the deleterious effects of the condition are reduced or eliminated.

Other aspects and features will be apparent and are pointed out hereinafter.

DETAILED DESCRIPTION OF THE INVENTION

Acronyms

PUFA is an abbreviation for polyunsaturated fatty acid.
SDA is an abbreviation for stearidonic acid.
EPA is an abbreviation for eicosapentaenoic acid.
DHA is an abbreviation for docosahexaenoic acid.
TNF is an abbreviation for tumor necrosis factor. Thus, TNF-α is tumor necrosis factor-α, etc.
IL is an abbreviation for interleukin. Thus, IL-1 is Interleukin-1, etc.

The terms "treating" and "to treat" as used herein mean to alleviate symptoms, eliminate the causation of an inflammatory disorder either on a temporary or a permanent basis, slow the appearance of symptoms and/or progression of the disorder, or prevent disease (i.e. to treat prophylactically). The term "treatment" includes alleviation, elimination of causation or prevention of an inflammatory disorder. For methods of prevention, a subject to be treated is generally an animal at risk for an inflammatory condition due to genetic predisposition, diet, exposure to disorder-causing agents, exposure to pathogenic agents, and the like.

The term "mammal," as used herein, refers to any animal classified as a mammal, including humans, domestic and farm animals, and zoo or companion animals, such as dogs, horses, cats, cattle, etc. Preferably, the mammal is a human.

The term "inflammatory disorder" as used herein, refers to any disorder that is either caused by inflammation or whose symptoms include inflammation. By way of example, an inflammatory disorder caused by inflammation may be a septic shock, and an inflammatory disorder whose symptoms include inflammation may be rheumatoid arthritis. The inflammatory disorders of the present invention include but are not limited to: cardiovascular disease, rheumatoid arthritis, multiple sclerosis, Crohn's disease, inflammatory bowel disease, systemic lupus erythematosis, polymyositis, septic shock, graft vs. host disease, asthma, rhinitis, psoriasis, cachexia associated with cancer, and eczema.

As used herein, the term "down-regulation," or "down-regulating," means to decrease a concentration of a biological substance, wherein such down-regulation may be achieved by any of the biological mechanisms, such as, e.g., inhibition of synthesis of the biological substance.

As used herein, an "effective amount" means the dose or amount to be administered to a patient, and the frequency of administration to the patient, which are readily determined by one of ordinary skill in the art by the use of known techniques and by observing results obtained under analogous circumstances to effectively treat a disease or condition given the principles elucidated herein. In determining the effective amount or dose, a number of factors are considered by an attending diagnostician, including but not limited to, the potency and duration of action of the compounds used; the nature and severity of the illness to be treated as well as the sex, age, weight, general health and individual responsiveness of the patient to be treated; and other relevant circumstances known to one skilled in the art.

The phrase "therapeutically-effective" indicates the capability of an agent to prevent, or improve the severity of, the disorder, while avoiding adverse side effects typically associated with alternative therapies. The phrase "therapeutically-effective" is to be understood to be equivalent to the phrase "effective for the treatment or prevention," and both are intended to qualify, e.g., the amount of stearidonic acid used in the methods of the present invention which will achieve the goal of improvement in the severity of an inflammatory disorder or preventing the disorder while avoiding adverse side effects typically associated with alternative therapies.

The term "pharmaceutically acceptable" is used herein to mean that a noun modified as such is appropriate for use in a particular pharmaceutical product. Pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

Pharmaceutically acceptable excipients include, but are not limited to, physiological saline, Ringer's, tocopherol, phosphate solution or buffer, buffered saline, and other carriers known in the art. Pharmaceutical compositions may also include stabilizers, anti-oxidants, colorants, and diluents. Pharmaceutically acceptable carriers and additives are chosen such that side effects from the pharmaceutical compound are minimized and the performance of the compound is not canceled or inhibited to such an extent that treatment is ineffective.

As used herein, n-3 PUFAs refers to an omega-3 polyunsaturated fatty acid, either naturally occurring or produced synthetically. It should be noted that various naming conventions exist for describing unsaturated fatty acids. For example, names such as α-linolenic acid are sometimes used to describe polyunsaturated fatty acids. Abbreviations, using three letter designations, such as ALA (for α-linolenic acid) are commonly used in the art to identify a polyunsaturated fatty acid. Another convention based on the position of the carbon in relation to the first double bond from the carboxylic moiety of the fatty acid uses the Greek symbol Δ (delta) to identify said carbon (e.g. $18:3\Delta^{9,12,15}$). The IUPAC nomenclature system also numbers the carbons from the carboxyl end of a fatty acid (e.g., cis 9,12,15-octadecatrienoic acid). At present, a more widely used convention uses the number of carbons in the chain, followed by a colon, and then the Greek symbol ω (omega) or the letter "n" to describe the first double bond from the methyl end. Thus, ALA (cis 9,12,15-octadecatrienoic acid) can also be represented as 18:3 ω-3 or 18:3, n-3 (eighteen carbons, three double bonds, the first double bond occurring at the third carbon from the methyl end). It should be understood that a name associated with a fatty acid herein is not intended to place a limitation thereon, and alternative nomenclature for describing a polyunsaturated fatty acid molecule, other than the name used herein, is intended to fall within the scope of the present invention.

Stearidonic acid (18:4, n-3) is an omega-3, polyunsaturated fatty acid, produced by the action of delta-6 fatty acid desaturase on α-linolenic acid (18:3, n-3). It is generally known in the art that intake of long omega-3 fatty acids such as eicosapentaenoic acid (EPA) and docosahexaenoic acid (DHA), which are found in fish and fish oil results in many health benefits. For example, certain benefits of omega-3 fats in cardiovascular disease are described, e.g., in Simopoulos, A. P., Can. J. Physiol. Pharmacol, 75:234 (1997). The tissue levels of EPA can be increased not only by ingestion of EPA but of α-linolenic acid (ALA), which is converted to EPA in the body by the action of delta-6 desaturase. However, this conversion is highly inefficient (Mantzioris et al., Dietary substitution with an α-linolenic acid-rich vegetable oil increases eicosapentaenoic acid concentrations in tissues, Am. J. Clin. Nutr.; 59:1304–1309 (1994)). The reason for this inefficiency is believed to lie in the fact that delta-6 desaturase is inefficient in vivo, thus making the conversion of ALA to EPA a rate-limiting reaction. Accordingly, in order to increase tissue levels of EPA, one would have to consume large amounts of ALA. However, applicants have discovered that consumption of just moderate amounts of SDA provides an efficient source of EPA. Applicants have determined that SDA is about four times more efficient than ALA at elevating tissue EPA levels in humans, thus determining the conversion properties of SDA to EPA in humans and further demonstrating potential health benefits for SDA. In the same studies, SDA administration was also able to increase the tissue levels of docosapentaenoic acid (DPA), which is an elongation product of EPA.

PUFAs may be found in a plant or microorganism as free fatty acids or in conjugated forms such as acylglycerols, phospholipids, sulfolipids or glycolipids, and may be extracted from the cell through a variety of means well-known in the art. Such means may include extraction with organic solvents, sonication, supercritical fluid extraction using for example carbon dioxide, and physical means such as presses, or combinations thereof. Of particular interest is extraction with methanol and chloroform. Where desirable, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high speed centrifugation or distillation, or combinations of these techniques. Protection of reactive groups, such as the acid or alkenyl groups, may be done at any step through known techniques, for example alkylation or iodination. Methods used include methylation of the fatty acids to produce methyl esters. Similarly, protecting groups may be removed at any step. Desirably, purification of fractions containing GLA, SDA, ARA, DHA and EPA may be accomplished by treatment with urea and/or fractional distillation.

For dietary supplementation, purified PUFAs, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents. Alternatively, PUFAs may be supplied to a subject wherein the subject consumes foods having elevated levels of SDA.

Stearidonic acid may be administered by feeding to a subject a plant, plant part(s), or foodstuffs derived therefrom. Such a plant may produce stearidonic acid naturally, or may be genetically engineered for increased SDA. Examples of such plants having increased SDA that may be used with the invention are described in U.S. Pat. No. 6,459,018, the disclosure of which is incorporated herein by reference.

For pharmaceutical use (human or veterinary), the compositions are generally administered orally but can be administered by any route by which they may be successfully absorbed, e.g., parenterally (i.e. subcutaneously, intramuscularly or intravenously), rectally or vaginally or topically, for example, as a skin ointment or lotion. The PUFAs of the present invention may be administered alone or in combination with a pharmaceutically acceptable carrier or excipient. Where available, gelatin capsules may be a preferred form of oral administration. Dietary supplementation as set forth above can also provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl. glucamine, found in PCT publication WO 96133155. The preferred esters are commonly ethyl esters. As solid salts, the PUFAs also can be administered in tablet form. For intravenous administration, the PUFAs or derivatives thereof may be incorporated into commercial formulations such as Intralipids. The typical normal adult plasma fatty acid profile comprises 6.64 to 9.46% of ARA, 1.45 to 3.11% of DGLA, and 0.02 to 0.08% of GLA. These PUFAs, or their metabolic precursors, can be administered, either alone or in mixtures with other PUFAs, to achieve a normal fatty acid profile in a patient. Where desired, the individual components of formulations may be individually provided in kit form, for single or multiple use. A dosage of a particular fatty acid may be from 0.1 mg to 20 g, or even 100 g daily. However, such amounts vary greatly between particular individuals. Those suffering from inflammatory disorders, such as rheumatoid arthritis, need particular amounts of certain PUFAs, such as SDA.

Applicants have discovered that consumption of SDA leads to a decrease in blood levels of proinflammatory cytokines TNF-α and IL-1β. Accordingly, the present invention provides methods for down-regulating TNF-α and/or IL-1β, as well as C-reactive protein. Such methods comprise, in one embodiment, administering to a mammal exhibiting elevated concentrations of TNF-α and/or IL-1β and/or C-reactive protein therapeutically effective amounts of SDA for a time period effective for the down-regulation TNF-α and/or IL-1β and/or C-reactive protein. This is the first demonstration that SDA can down-regulate these cytokines. The instant invention also involves the administration of therapeutically effective amounts of stearidonic acid to subjects who may not be exhibiting higher than normal concentrations of TNF-α and/or IL-1β and/or C-reactive protein, but who are at risk of developing an inflammatory disorder. Such therapeutically effective amounts will be apparent to one skilled in the art based on the results disclosed herein.

Concentrations of TNF-α and IL-1β and/or C-reactive protein in humans not subject to an inflammatory disorder are known in the medical sciences and/or can be easily determined without undue experimentation. For other mammals, the normal concentrations of these two cytokines are either known in the art or can be determined by one of ordinary skill in the art without undue experimentation.

Higher than normal concentrations of TNF-α and/or IL-1β and/or C-reactive protein in a patient may often result from an inflammatory disorder, including but not limited to: cardiovascular disease, rheumatoid arthritis, multiple sclerosis, Crohn's disease, inflammatory bowel disease, systemic lupus erythematosis, polymyositis, septic shock, graft vs. host disease, asthma, rhinitis, psoriasis, cachexia associated with cancer, and eczema. In a preferred embodiment, the treated inflammatory disorders comprises cardiovascular disease and rheumatoid arthritis, and more preferably the cardiovascular disease treated is atherosclerosis.

The amount of SDA that is therapeutically effective depends on multiple factors, such as the seriousness of inflammatory disorder being treated, dietary habits of a patient, the age of the patient, presence of additional conditions, etc. A subject that consumes relatively small amounts of SDA in their normal diet will need a greater amount than one who typically consumes a greater amount of SDA. One skilled in the art would know how to determine the therapeutically effective amount for a patient based on these considerations.

The therapeutically effective time period can vary significantly depending on the disorder of a patient. Thus, an inflammation that is a result of a bacterial infection may require less time to be treated than a chronic or a life-long condition. For example, a chronic disorder such as rheumatoid arthritis may require a longer treatment than septic shock. The length of treatment can be determined by one skilled in the art without undue experimentation. One skilled in the art may use the assay of the instant invention, as discussed below; in determining a therapeutically effective time.

Those skilled in the art will appreciate that dosages may also be determined with guidance from Goodman & Goldman's The Pharmacological Basis of Therapeutics, Ninth Edition (1996), Appendix II, pp. 1707–1711. However, the therapeutically effective amount of stearidonic acid that can be administered to a patient with elevated TNF-α and/or IL-1β and/or C-reactive protein generally should range from about 0.1 g/day to about 10 g/day. Preferably, said therapeutic amounts are from about 0.25 g/day to about 8 g/day. More preferably, said therapeutic amounts are from about 0.5 g/day to about 5 g/day. Most preferred, said therapeutic amount is about 1.5 g/day.

The particular dosage will vary generally within this range, depending upon the dosage form employed and the route of administration utilized. The exact formulation; route of administration and dosage can be chosen by the individual physician in view of the patient's condition. (See e.g., Fingl et al., 1975, in "The Pharmacological Basis of Therapeutics," Ch. 1, p.1).

SDA can be administered to a patient via parenteral and enteral routes. Parenteral administration includes subcutaneous, intramuscular, intradermal, intramammary, intravenous, and other administrative methods known in the art. Enteral administration includes solution, tablets, sustained release capsules, enteric coated capsules, and syrups. When administered, the pharmaceutical composition may be at or near body temperature.

In a preferred embodiment, SDA is administered orally via ingestion of foodstuffs enriched in stearidonic acid. Foodstuffs that may be utilized to practice the present invention include, but are not limited to: beverages, (including soft drinks, carbonated beverages, ready to mix beverages and the like), infused foods (e.g. fruits and vegetables), sauces, condiments, salad dressings, fruit juices, syrups, desserts (including puddings, gelatin, icings and fillings, baked goods, and frozen desserts such as ice creams and sherbets), chocolates, candies, soft frozen products (such as soft frozen creams, soft frozen ice creams and yogurts, soft frozen toppings, such as dairy or non-dairy whipped toppings), oils and emulsified products (such as shortening, margarine, mayonnaise, butter, cooking oil, and salad dressings), prepared meats (such as sausage), intermediate moisture foods, (e.g. rice and dog foods) and the like.

Foodstuffs can be enriched in SDA by conventional methods such as obtaining SDA and evenly distributing it throughout the foodstuff, to which it is added by dissolution, or by suspension, or in an emulsion. For example, SDA can be dissolved in an edible solubilizing agent, or can be mixed with an edible solubilizing agent, an effective amount of a dispersant, and optionally, an effective amount of an antioxidant. Examples of useful antioxidants include, but are not limited to, tocopherols, such as α-tocopherol, ascorbic acid, inexpensive synthetic antioxidants, and mixtures thereof. Foodstuffs may also be prepared from transgenic plants engineered for increased SDA. Examples of such plants having increased SDA that may be used with the invention are described in U.S. Pat. No. 6,459,018, the disclosure of which is incorporated herein by reference.

Effective carriers for preparing emulsions or suspensions include water, alcohols, polyols and mixtures thereof. Examples of useful dispersants include, but are not limited to, lecithin, other phospholipids, sodium lauryl sulfate, fatty acids, salts of fatty acids, fatty acid esters, other detergent-like molecules, and mixtures thereof. Alternatively, the foodstuff can be made by a method comprising obtaining SDA and mixing it with an edible solubilizing agent and an effective amount of a dispersant. Again, the edible solubilizing agent can include, but is not limited to, monoglycerides, diglycerides, triglycerides, vegetable oils, tocopherols, alcohols, polyols, or mixtures thereof, and the dispersant can include, but is not limited to, lecithin, other phospholipids, sodium lauryl sulfate, fatty acids, salts of fatty acids, fatty acid esters, other detergent-like molecules, and mixtures thereof.

The ability to down-regulate TNF-α and/or IL-1β by consuming SDA demonstrates the potential of using SDA to treat and prevent inflammatory disorders. Accordingly, the invention further provides methods for treating an inflammatory disorder in a mammal in need of such treatment, wherein said method comprises administering to the mammal therapeutically-effective amounts of stearidonic acid for a therapeutically-effective time period. The invention also provides methods for preventing an inflammatory disease by administering a therapeutically-effective amount of SDA to a mammal at risk to develop an inflammatory disease. Mammals at risk to develop an inflammatory disease are easily identified by one skilled in the art and do not require undue experimentation.

In one embodiment, said inflammatory disorder comprises cardiovascular disease, rheumatoid arthritis, multiple sclerosis, Crohn's disease, inflammatory bowel disease, systemic-lupus erythematosis, polymyositis, septic shock, graft vs. host disease, asthma, rhinitis, psoriasis, cachexia associated with cancer, and eczema. Preferably, the inflammatory disorders comprise cardiovascular disease and rheumatoid arthritis, and more preferably said cardiovascular disease is atherosclerosis. In another preferred embodiment, the mammal is a human who is in need of treatment or prevention of an inflammatory disorder. A mammal in need of treatment will be recognized by one skilled in the art, as will a mammal in need of prevention of an inflammatory disorder.

It is another object of the present invention to provide a method wherein therapeutically effective amount of stearidonic acid is administered to patients in need of treatment of or prevention from an inflammatory disorder. In one preferred embodiment, said therapeutic amount comprises an amount effective at decreasing the blood concentration of proinflammatory cytokines. In one embodiment, the proinflammatory cytokines comprise TNF-α and IL-1β. In another embodiment, it is the concentration of TNF-α that is down-regulated, and in yet another embodiment, IL-1β concentration is down-regulated.

In another embodiment, the therapeutic amounts of SDA range from about 0.1 g/day to about 10 g/day. More preferably, the therapeutic amounts of SDA range from about 0.25 g/day to about 8 g/day. Even more preferably, the therapeutic amounts of SDA range from about 0.5 g/day to about 5 g/day. Most preferably, the therapeutic amounts are about 1.5 g/day. It should be noted that the dosage form and amount of SDA to be administered can readily be established by reference to known treatments involving EPA or prophylactic regimens. As mentioned previously, the amount of SDA that is administered and the dosage regimen for treating an inflammatory disorder with SDA depends on a variety of factors, and thus may vary widely. The dosage will generally be lower if the compounds are administered locally rather than systemically, and for prevention rather than for treatment. Such treatments may be administered as often as necessary and for the period of time judged necessary by a treating physician. One of skill in the art will appreciate that the dosage regime or therapeutically effective amount of SDA may need to be optimized for each individual and can be determined without undue experimentation.

The present invention also provides a method for down-regulating proinflammatory cytokines by administering therapeutically effective amounts of SDA. The proinflammatory cytokines down-regulated include TNF-α and IL-1β. Such therapeutically effective amounts of SDA may be obtained by a mammal in need thereof through the consumption of foods with elevated levels of SDA.

The present invention further provides methods for altering eicosapentaenoic acid level in a human, wherein said method comprises administering therapeutically effective amounts of SDA to said human, wherein said human metabolizes said SDA to EPA, resulting in altered levels of EPA. Metabolism of SDA to EPA occurs through chain elongation to a 20:4 (n-3) fatty acid, followed by desaturation of the elongated product by delta-5 desaturase. In addition, administration of SDA to a mammal takes advantages of "physiological channeling," wherein the metabolism of SDA to EPA and DHA is ultimately controlled by the body's fatty acid metabolism. Thus, this metabolic control is likely to result in a more efficacious distribution of EPA and DHA in lipid pools than that provided by direct administration of EPA and/or DHA.

In one embodiment, altered EPA levels are present in tissues selected from the group consisting of erythrocyte phospholipids, platelet phospholipids, mononuclear cell phospholipids, plasma phospholipids, triglycerides, and cholesterol levels. However, EPA levels may also be altered in membranes of other cells in the body. Thus, altered EPA levels in tissues other than the ones listed herein are also contemplated as falling within the scope of the present invention.

In another embodiment, the therapeutically effective amount of SDA administered to alter EPA levels is in the range from about 0.1 g/day to about 10 g/day. Preferably, said therapeutic amounts are from about 0.25 g/day to about 8 g/day. More preferably, said therapeutic amounts are from about 0.5 g/day to about 5 g/day. Most preferred, said therapeutic amount is about 1.5 g/day.

Administration of SDA in combination with other therapies that are clinically used to treat inflammatory disorders, such as those discussed above in the Background section, are also contemplated within the scope of the present invention. By way of example, SDA may be administered in combination with a corticosteroid or an immuno-suppressant to treat inflammatory disorders that are also autoimmune in origin. SDA may be administered with anti-inflammatory medications or nutritional supplements, such as those administered to suppress COX-II. SDA may also be administered with other therapeutic treatments not directed towards the treatment of inflammatory disorders.

The instant invention also involves an assay comprising an analysis of blood and/or tissue from a subject to determine the presence, absence or quantity of TNF-α and/or IL-1β in a subject; wherein said analysis is performed in conjunction with, i.e., before, during, or after stearidonic acid (18:4, n-3) administration to a subject. The assay of the instant invention is characterized by the link between consumption of SDA and the proinflammatory markers, TNF-α and IL-1β. The link is characterized by the discovery that SDA may be administered in therapeutically effective amounts via the typical Western diet and down-regulate TNF-α and IL-1β.

An analysis of the TNF-α and/or IL-1β levels in a subject may be performed and one skilled in art can then determine whether the administration of therapeutic amounts of stearidonic acid is necessary or desired. If a subject is already on a regimen of SDA, the assay may be used to optimize the amount of SDA required to treat or prevent an inflammatory disorder. Notably, applicants have determined that the therapeutically effective amount of stearidonic acid generally will equal approximately four times the therapeutically effective amount of EPA. In one preferred embodiment, the assay is performed on a subject in need of treatment or prevention of an inflammatory disorder. Said subject is then given a diet containing therapeutically effective amounts of stearidonic acid. The assay may be performed on the subject a second time to determine the efficacy of the therapeutic amount of stearidonic acid. The assay of the present invention may also be used for experimental or research purposes for determining a therapeutically effective amount of SDA.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the present invention.

All publications and patent applications cited in this specification are herein incorporated by reference as if each individual publication or patent application was specifically and individually indicated to be incorporated by reference.

EXAMPLES

The following examples are presented by way of illustration, not of limitation.

Example 1

Subjects and Methods 45 males and post-menopausal female—19–65 years of age, normolipidemic, and with a body mass index (BMI) in the range 20 to 30, were recruited. Exclusion criteria included bleeding disorders, hypertension, inflammatory disorders, active gastrointestinal diseases, chronic use of low dose aspirin, consumption of restaurant or takeaway evening meals more than twice per week, use of dietary supplements rich in n-3 or n-6 fatty acids, habitual consumption of more than 1 fish meal per month, and plasma phospholipid EPA+DHA levels>7.9% of total fatty acids (level achieved in the study group was 4.9±1.0% of total fatty acids).

Subjects were randomly allocated to one of three groups, designated ALA, SDA, and EPA.

A. Study Design

Following a 3-week run-in period, subjects ingested either ALA, SDA, EPA supplied as ethyl esters in capsules. Intakes were 0.75 g/day for 3 weeks followed by 1.5 g/day for the subsequent 3 weeks.

TABLE 1

Study Design

| Weeks | −3 | 0 | 3 | 6 |
|---|---|---|---|---|
| Visit | 1 | 2 | 3 | 4 |
|  | Run-in | 0.75 g/d |  | 1.5 g/d |

At each visit, 36 mL of blood was taken by venepuncture after an overnight fast. Blood was aliquoted into various tubes for the following procedures.

B. Cell Separations and Fatty Acid Analysis

Blood (20 mL) was added to tubes containing 4 mL 4.5% EDTA in water and 4 mL—6% dextran in normal saline, pH 7.0. Erythrocytes were allowed to sediment under gravity at 37° C. for 30 min. The leucocyte-rich plasma was layered onto LYMPHOPREP, density 1.077 (Nycomed Pharma, Oslo) and centrifuged at 110 g for 10 min to separate leucocytes from the platelets, which were removed. The gradient was further centrifuged at 200 g for 20 min to separate the neutrophils from mononuclear cells, which were removed.

Samples were processed for fatty acid analysis as described in Mantzioris et al., *Am. J. Clin. Nutr.*, 72:42–8 (2000). Plasma, washed platelet and mononuclear cell pellets were stored at −80° C. Erythrocyte pellets were treated fresh with chloroform:isopropanol (2:1) and the lipid extracts stored at 4° C. Plasma, platelet and mononuclear cell pellets were extracted with chloroform:methanol. The cellular and plasma lipid extracts were fractionated by thin-layer chromatography. For the cellular extracts, the phospholipid fraction was retained and for the plasma extracts, the phospholipid, cholesterol ester, and triglyceride fractions were retained. These were transesterified by methanolysis (1% $H_2SO_4$ in methanol at 70° C. for 3 h). Fatty acid methyl esters were separated and quantified with a HEWLETT-PACKARD 6890 gas chromatograph equipped with a 50 m capillary column coated with BPX-70 (0.25 μm film thickness; SGE Pty Ltd, Victoria, Australia) (see Mantzioris et al., supra). Fatty acid standards were obtained from NuChek Prep Inc. (Elysian, Minn.) and included stearidonic acid obtained from Sigma Aldrich Pty Ltd. (Castle Hill, NSW, Australia). All organic solvents contained butylated hydroxy anisole (0.005%) as an antioxidant.

C. Eicosanoid and Cytokine Synthesis

Blood (4 mL) was added to heparinised tubes, bacterial lipopolysaccharide (LPS) was added (200 ng/mL), and the mixture was incubated at 37° C., 5% $CO_2$, for 24 h. Plasma was collected and assayed for prostaglandin $E_2$ ($PGE_2$) by radioimmunoassay (RIA), interleukin-1β (IL-1β) and tumor necrosis factor-α (TNF-α) by ELISA, as described in Mantzioris et al., supra.

Blood (4 mL) was collected in a clotting tube, incubated at 37° C. for 1 h, and serum was assayed for thromboxane $B_2$ ($TXB_2$) by RIA as described (see Mantzioris et al., supra). $TXB_2$ is the stable hydrolysis product of $TXA_2$.

D. Plasma Lipids

Blood (4 mL) was collected in heparinised tubes, and plasma total cholesterol, LDL and HDL cholesterol, and plasma triglycerides were measured in the clinical diagnostic laboratories of the Royal Adelaide Hospital/Institute of Medical and Veterinary Science (IMVS).

E. Diet

Subjects were instructed in avoiding dietary n-6 fatty acids and substituting monounsaturated (n-9) fatty acids where possible. To facilitate this pattern of intake, subjects were provided with salad dressing, cooking oil, and spread, all of which were low in n-6 fatty acids and high in monounsaturated (n-9) fatty acids. Subjects were provided with diet diaries and instructed in making weighed food records on designated days (weekdays and weekend days).

F. Dietary Intake

Diet diaries were analyzed using the Diet/1 program to provide macronutrient (carbohydrate, protein, fat, alcohol, P:S ratio) intake data. This program uses the Australian NUT-TAB database. This analysis also provides intake data on omega-6 and omega 9 fatty acids.

G. Statistical Analysis

For comparisons between visits within each group, repeated measures ANOVA followed by Newman-Keuls multiple comparisons test was used (Kwikstat, TexaSoft, Cedar Hill, Tex.). For comparisons between groups at each visit, ANOVA followed by Newman-Keuls multiple comparisons test was used (Kwikstat).

Example 2

Results

There was no statistically significant difference in baseline BMI between the groups (Table 1). Subjects were weighed at each visit and there was no significant change in weight during the trial.

TABLE 2

BMI

| Dietary Group | Value ($Kg/m^2$) |
|---|---|
| EPA | $(25.6 \pm 3.0^1$ |
| SDA | $26.2 \pm 3.8$ |
| ALA | $27.5 \pm 2.9$ |

[1]mean ± SD

Summary data for energy and macronutrient intake are shown in Table 2. There was no significant difference in energy or macronutrient intake between any group at baseline (Diet Record period 1). There were no statistically significant changes in energy or macronutrient intake during the study (i.e. Diet Record periods 1 to 3) in any group.

TABLE 3

Energy and Macronutrient Intake estimated from weighed food records.

| | Group | Diet Record Period[1] | | |
|---|---|---|---|---|
| | | 1 | 2 | 3 |
| Energy MJ [Kcal] | EPA | $8.99 \pm 1.91^2$ [2161] | $9.45 \pm 1.91$ [2272] | $9.34 \pm 1.98$ [2245] |
| | SDA | $8.97 \pm 2.08$ [2157] | $9.12 \pm 2.48$ [2192] | $9.26 \pm 21.4$ [2226] |
| | ALA | $8.80 \pm 1.29$ [2114] | $9.06 \pm 2.04$ [2178] | $8.77 \pm 1.71$ [2107] |
| Protein g [% en] | EPA | $99 \pm 23$ [18.2] | $107 \pm 22$ [18.4] | $101 \pm 23$ [17.7] |
| | SDA | $91 \pm 20$ [16.5] | $91 \pm 24$ [16.1] | $91 \pm 27$ [15.7] |

TABLE 3-continued

Energy and Macronutrient Intake estimated from weighed food records.

| | | Diet Record Period[1] | | |
|---|---|---|---|---|
| | Group | 1 | 2 | 3 |
| | ALA | 97 ± 24 | 98 ± 22 | 95 ± 25 |
| | | [17.7] | [17.5] | [17.5] |
| Carbohydrate g | EPA | 256 ± 64 | 264 ± 70 | 272 ± 82 |
| [% en] | | [48.4] | [47.5] | [49.0] |
| | SDA | 269 ± 80 | 267 ± 88 | 274 ± 70 |
| | | [50.6] | [49.2] | [50.5] |
| | ALA | 239 ± 55 | 247 ± 63 | 257 ± 67 |
| | | [46.2] | [46.6] | [49.6] |
| Fat Total g | EPA | 75 ± 22 | 82 ± 26 | 82 ± 18 |
| [% en] | | [30.9] | [32.3] | [32.7] |
| | SDA | 75 ± 20 | 78 ± 22 | 78 ± 25 |
| | | [30.9] | [32.2] | [31.0] |
| | ALA | 73 ± 16 | 80 ± 36 | 67 ± 18 |
| | | [30.5] | [31.6] | [28.1] |
| Fat n-6 g | EPA | 7.3 ± 2.2 | 8.0 ± 3.4 | 8.6 ± 4.8 |
| [% en] | | [3.0] | [3.1] | [3.4] |
| | SDA | 7.2 ± 2.5 | 6.3 ± 2.0 | 6.7 ± 1.8 |
| | | [2.9] | [2.6] | [2.7] |
| | ALA | 7.0 ± 2.6 | 6.7 ± 2.8 | 6.2 ± 2.0 |
| | | [2.9] | [2.7] | [2.6] |
| Fat Mono g | EPA | 28.1 ± 10.4 | 30.5 ± 11.7 | 28.0 ± 7.9 |
| [% en] | | [11.4] | [11.8] | [11.2] |
| | SDA | 27.9 ± 7.3 | 28.8 ± 9.4 | 29.0 ± 11.0 |
| | | [11.6] | [11.9] | [11.5] |
| | ALA | 27.4 ± 8.4 | 29.9 ± 13.9 | 25.0 ± 7.4 |
| | | [11.4] | [11.7] | [10.5] |
| Fat Sat g | EPA | 33.3 ± 113 | 36.9 ± 11.2 | 38.0 ± 8.7 |
| [% en] | | [13.6] | [14.6] | [15.2] |
| | SDA | 33-0 ± 9.6 | 36.1 ± 10.7 | 35.6 ± 12.0 |
| | | [13.61] | [14.9] | [14.2] |
| | ALA | 31.4 ± 8.9 | 36.0 ± 18.8 | 29.5 ± 9.9 |
| | | [13.3] | [14.3] | [12.3] |

[1]Diet Record period 1 = period between −3 to 0 weeks (run-in)
[1]Diet Record period 2 = period between 0 to 3 weeks (0.75 g fatty acid)
[1]Diet Record period 3 = period between 3 to 6 weeks (1.5 g fatty acid)
[2]mean ± SD Returned capsule count was used to assess compliance for capsule intake. Compliance was high and there was no difference between the dietary groups in either of the dietary periods (Table 4).

TABLE 4

Compliance

| Dietary Group | Weeks 0 to 3 (0.75 g test fatty acid) | Weeks 3 to 6 (1.5 g test fatty acid) |
|---|---|---|
| EPA | 100.0 ± 4.1[1] | 98.5 ± 8.4 |
| SDA | 100.3 ± 3.8 | 100.5 ± 2.6 |
| ALA | 100.5 ± 4.2 | 98.5 ± 5.2 |

[1]% compliance; mean ± SD

With regard to fatty acids, at baseline, there was no significant difference between the dietary groups in EPA concentration in erythrocyte or plasma phospholipids. Ingestion of EPA or SDA at 0.75 g/day (weeks 0 to 3) or 1.5 g/day (weeks 3 to 6) significantly increased EPA concentration in the phospholipid fractions of erythrocytes and plasma (Table 5). Ingestion of ALA at 1.5 g/day, but not at 0.75 g/day significantly increased EPA concentrations (Table 5). Similar results were observed for EPA concentrations in platelets and mononuclear cell phospholipids, plasma cholesterol esters, and plasma triglycerides.

TABLE 5

EPA (% of total fatty acids)

| Fraction | Group | Visit No. 1 | 2 | 3 | 4 |
|---|---|---|---|---|---|
| Red Blood | A | 0.85 (0.16)[a] | 0.81 (0.14)[a] | 1.60 (0.31)[b1] | 2.56 (0.65)[c1] |
| | B | 1.00 (0.22)[a] | 0.96 (0.19)[a] | 1.16 (0.17)[b2] | 1.44 (0.24)[c2] |
| | C | 0.88 (0:16)[a] | 0.88 (0.17)[a] | 0.92 (0.23)[a3] | 1.01 (0.18)[b3] |
| Platelet | A | 0.44 (0.12)[a] | 0.45 (0.09)[a] | 1.08 (0.26)[b1] | 1.68 (0.43)[c1] |
| | B | 0.55 (0.20)[a] | 0.54 (0.18)[a] | 0.72 (0.17)[ab2] | 0.87 (0.30)[b2] |
| | C | 0.44 (0.12)[a] | 0.48 (0.11)[a] | 0.55 (0.14)[a2] | 0.64 (0.21)[b2] |
| Monocyte | A | 0.66 (0.32)[a] | 0.52 (0.11)[a] | 1.38 (0.35)[b1] | 2.25 (0.74)[c1] |
| | B | 0.70 (0.17)[a] | 0.61 (0.13)[a] | 0.85 (0.16)[b2] | 1.12 (0.30)[c2] |
| | C | 0.67 (0.20)[a] | 0.57 (0.11)[a] | 0.63 (0.14)[a3] | 0.81 (0.28)[b2] |
| Plasma Phospholipid | A | 1.10 (0.40)[a] | 1.04 (0.23)[a] | 2.71 (0.71)[b1] | 4.48 (1.35)[c1] |
| | B | 1.19 (0.21)[a] | 1.27 (0.30)[a] | 1.80 (0.28)[b2] | 2.38 (0.51)[c2] |
| | C | 1.07 (0.23)[a] | 1.16 (0.31)[ab] | 1.33 (0.54)[bc3] | 1.43 (0.40)[c3] |
| Plasma CE | A | 1.03 (0.34)[a] | 1.02 (0.20)[a] | 2.95 (0.74)[b1] | 4.53 (1.31)[c1] |
| | B | 1.17 (0.26)[a] | 1.23 (0.29)[a] | 1.81 (0.39)[b2] | 2.37 (0.65)[c2] |
| | C | 1.11 (0.26)[a] | 1.16 (0.33)[ab] | 1.35 (0.58)[bc2] | 1.41 (0.36)[c3] |

TABLE 5-continued

EPA (% of total fatty acids)

| Fraction | Group | Visit No. | | | |
|---|---|---|---|---|---|
| | | 1 | 2 | 3 | 4 |
| Plasma TG | A | 0.31 (0.15)$^a$ | 0.27 (0.09)$_a$ | 0.73 (0.20)$_{b1}$ | 1.23 (0.47)$_{c1}$ |
| | B | 0.32 (0.10)$^a$ | 0.29 (0.11)$_a$ | 0.46 (0.18)$_{b2}$ | 0.63 (0.32)$_{c2}$ |
| | C | 0.26 (0.08) | 0.27 (0.12) | 0.32 (0.13)$_2$ | 0.34 (0.16)$_2$ |

Different letters indicate differences between visits - Repeated measures ANOVA
Different numbers indicate differences between groups - ANOVA
No letters or numbers - no significant differences
Visit 1 Beginning of Run-in (−3 weeks)
Visit 2 Baseline (0 weeks)
Visit 3 After 3 weeks on 0.75 g fatty acid (3 weeks)
Visit 4 After 3 weeks on 1.5g fatty acid (6 weeks)

Ingestion of EPA at 0.75 g/day or 1.5 g/day significantly increased DPA concentration in the phospholipid fractions of erythrocytes and plasma (Table 6). Ingestion of SDA at 1.5 g/day, but not at 0.75 g/day significantly increased DPA concentrations (Table 6). Similar results were observed for DPA concentrations in platelets and mononuclear cell phospholipids, plasma cholesterol esters, and plasma triglycerides.

TABLE 6

DPA (% of total fatty acids)

| | Group | Week | | | |
|---|---|---|---|---|---|
| | | −3 | 0 | 3 | 6 |
| Erythrocyte phospholipid | EPA | 2.92 ± 0.45$^{a1,2}$ | 2.81 ± 0.24$^a$ | 3.19 ± 0.30$^b$ | 3.71 ± 0.38$^c$ |
| | SDA | 3.31 ± 0.30$^{ab}$ | 3.16 ± 0.22$^b$ | 3.27 ± 0.27$^{ab}$ | 3.46 ± 0.29$^a$ |
| | ALA | 3.10 ± 0.40 | 3:08 ± 0:35 | 3.08 ± 0.37 | 3.19 ± 0.38 |
| Plasma phospholipid | EPA | 1.31 ± 0.29$^a$ | 1.34 ± 0.22$^a$ | 2.02 ± 0.45$^b$ | 2.46 ± 0.48$^c$ |
| | SDA | 1.37 ± 0.23$^a$ | 1.45 ± 0.19$^a$ | 1.68 ± 0.30$^b$ | 1.85 ± 0.34$^c$ |
| | ALA | 1.29 ± 0.18$^a$ | 1.39 ± 0.26$^{ab}$ | 1.38 ± 0.18$^{ab}$ | 1.46 ± 0.34$^b$ |

[1] mean ± SD
[2] Different letters indicate differences between visits; p < 0.05.

None of the dietary test fatty acids at either dose caused an increase in DHA concentrations compared to baseline. There was a slight, but statistically significant decrease in erythrocyte DHA with ingestion of the higher dose of EPA and ALA (Table 7). Otherwise, there were no significant changes in DHA concentrations in any cell type or plasma fraction. It is generally known in the art that consumption of ALA or EPA will not lead to the increases in tissue DHA, hence it is not surprising that SDA administration does not lead to elevated tissue levels of DHA.

TABLE 7

DHA (% of total fatty acids)

| | Group | Week | | | |
|---|---|---|---|---|---|
| | | −3 | 0 | 3 | 6 |
| Erythrocyte phospholipid | EPA | 5.02 ± 0.89$^{a1,2}$ | 4.62 ± 0.69$^b$ | 4.49 ± 0.68$^b$ | 4.22 ± 0.68$^c$ |
| | SDA | 4.65 ± 1.10$^a$ | 4.23 ± 0.86$^b$ | 4.08 ± 0.77$^b$ | 3.96 ± 0.74$^b$ |
| | ALA | 4.87 ± 0.74$^a$ | 4.61 ± 0.71$^b$ | 4.38 ± 0.66$^c$ | 4.28 ± 0.56$^c$ |
| Plasma | EPA | 3.97 ± 1.06$^a$ | 3.75 ± 0.77$^{ab}$ | 3.65 ± 0.72$^{ab}$ | 3.48 ± 0.64$^b$ |

TABLE 7-continued

DHA (% of total fatty acids)

| | | Week | | | |
|---|---|---|---|---|---|
| | Group | −3 | 0 | 3 | 6 |
| phospholipid | SDA | 3.40 ± 0.73 | 3.40 ± 0.79 | 3.27 ± 0.78 | 3.26 ± 0.63 |
| | ALA | 3.70 ± 0.63 | 3.64 ± 0.65 | 3.54 ± 0.63 | 3.39 ± 0.51 |

[1]mean ± SD
[2]Different letters indicate differences between visits; p < 0.05.

Figure 1A:
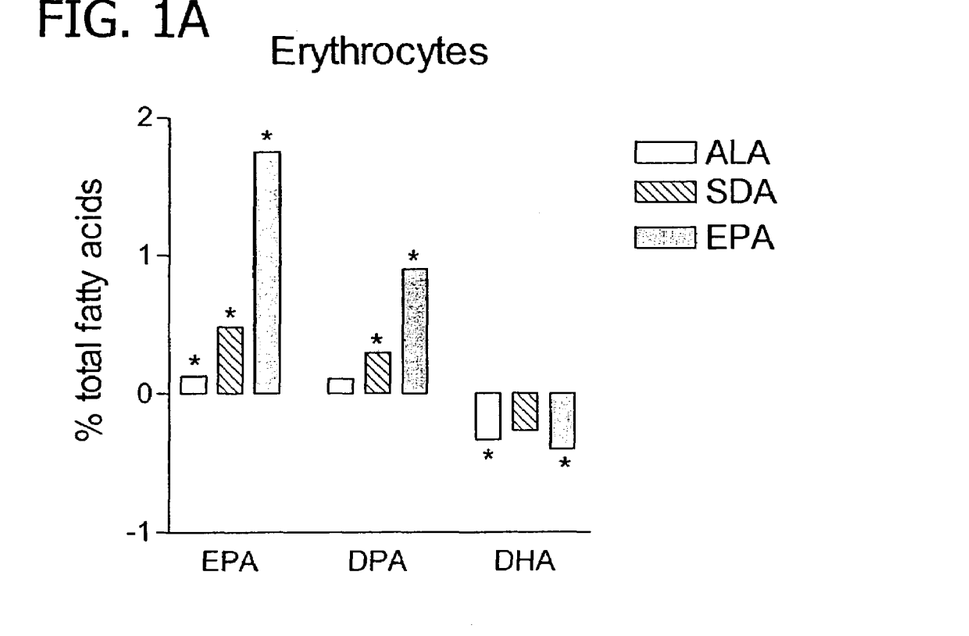
FIG. 1A depicts the changes in long chain n-3 fatty acids in erythrocytes and FIG. 1B depicts the same in plasma phospholipids resulting from ingestion of 1.5 g/day of the test fatty acids, EPA, SDA, and ALA. "*" indicates significantly different values from the baseline value for each fatty acid, $p<0.05$.
Figure 1B:
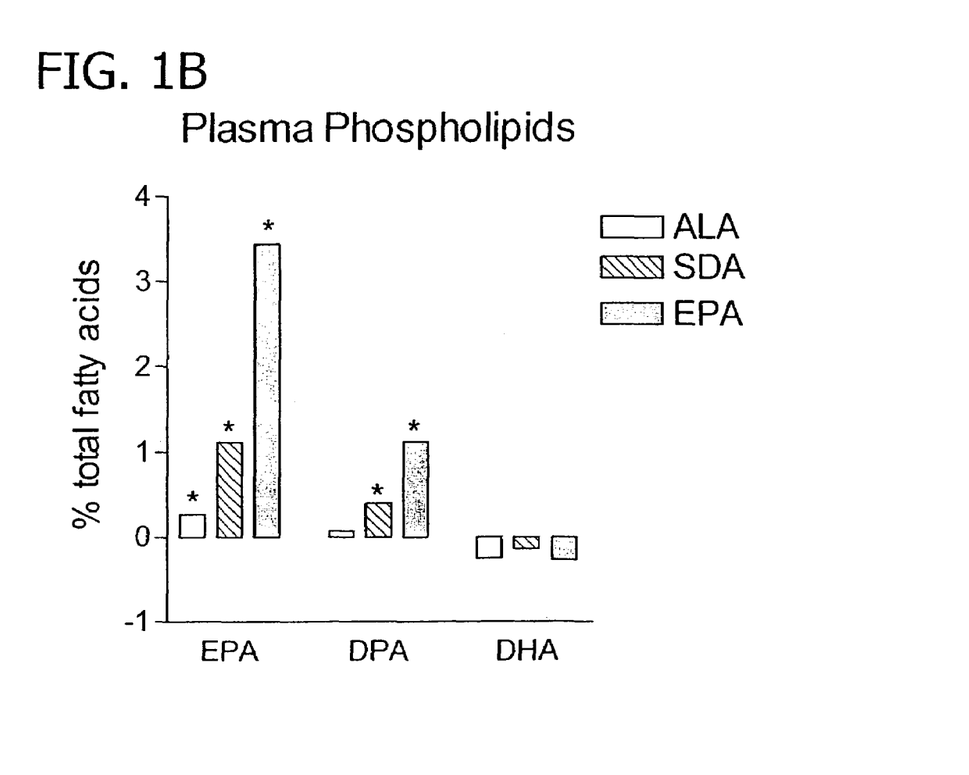

When tissue levels of the long-chain n-3 fatty acids were examined, SDA elevated EPA and DPA, but not DHA (FIG. 1). This pattern was seen also with ingestion of EPA where tissue levels of EPA and DPA were elevated, and DHA levels were decreased. With ingestion of ALA at 1.5 g/day, tissue levels of EPA, but not DPA were significantly elevated (FIG. 1).

At the 1.5 g/day dose, SDA was 3.7 to 4.1-fold more effective than ALA, and EPA was 3.1 to 3.6-fold more effective than SDA, in elevating EPA levels in erythrocyte and plasma phospholipids.

There were statistically significant decreases in LPS-stimulated TNF synthesis with ingestion of 1.5 g/day, but not with 0.75 g/day of ALA or SDA or EPA (Table 8).

TABLE 8

TNF-α synthesis in LPS-treated whole blood.

| Dietary | Week | | | |
|---|---|---|---|---|
| Group | −3 | 0 | 3 (ng/mL) | 6 |
| EPA | 36.6 ± 16.53[a1,2] | 38.9 ± 12.5[a] | 32.0 ± 11.8[ab] | 27.6 ± 10.6[b] |
| SDA | 37.6 ± 14.6[ab] | 43.7 ± 18.7[a] | 37.7 ± 14.2[ab] | 34.1 ± 12.0[b] |
| ALA | 30.9 ± 13.1[a] | 36.8 ± 17.4[a] | 32.7 ± 11.9[a] | 25.3 ± 7.2[b] |

[1]mean ± SD
[2]Different letters indicate differences between visits; p < 0.05.

Ingestion of 0.75 g/day or 1.5 g/day of SDA or EPA significantly decreased LPS-stimulated IL-1β synthesis. There was no effect of ALA at either dose (Table 9).

TABLE 9

IL-1β synthesis in LPS-treated whole blood.

| Dietary | Week | | | |
|---|---|---|---|---|
| Group | −3 | 0 | 3 (ng/mL) | 6 |
| EPA | 93.1 ± 26.8[a1,b] | 92.0 ± 25.4[a] | 75.3 ± 27.6[b] | 73.5 ± 16.4[b] |
| SDA | 106.9 ± 33.0[a] | 94.7 ± 29.3[b] | 81.4 ± 21.9[c] | 77.8 ± 26.4[c] |
| ALA | 97.9 ± 27.4 | 96.9 ± 30.9 | 87.3 ± 29.9 | 83.3 ± 24.0 |

[1]mean ± SD
[2]Different letters indicate differences between visits; p < 0.05.

The test fatty acids had no consistent effect on LPS-stimulated $PGE_2$ synthesis. This can be concluded from the fact that groups treated with ALA and SDA showed statistically significant increases in $PGE_2$ at Visit 3 following ingestion of 0.75 g of test articles, however no change was seen in $PGE_2$ in patients that were given 1.5 g/day of either fatty acid. There was no effect of EPA at either dose.

TABLE 10

$PGE_2$ synthesis in LPS-stimulated whole blood.

| Dietary | Week | | | |
|---|---|---|---|---|
| Group | −3 | 0 | 3 (ng/mL) | 6 |
| EPA | 3.78 ± 1.95[1,2] | 4.21 ± 1.59 | 5.05 ± 2.16 | 4.46 ± 1.47 |
| SDA | 3.97 ± 1.48[a] | *4.64 ± 1.09[a] | 6.26 ± 2.56[b] | 4.61 ± 0.95[a] |
| ALA | 4.00 ± 1.65[a] | 4.63 ± 2.21[a] | 6.25 ± 3.00[b] | 4.30 ± 1.37[a] |

[1]mean ± SD
[2]Different letters indicate differences between visits; p < 0.05.

$TXA_2$ synthesis during blood clotting was not affected by any of the test fatty acids.

There were no significant differences between groups at any visit or between visits for any group for fasting triglycerides, total cholesterol, LDL cholesterol, or HDL cholesterol.

In light of the detailed description of the invention and the examples presented above, it can be appreciated that the several aspects of the invention are achieved.

Example 3

Clinical Study of the Effectiveness of SDA on Down-Regulating C-Reactive Protein Approximately 35–50 males and post-menopausal female -19–65 years of age, normolipidemic, and with a body mass index (BMI) in the range 20 to 30, are recruited. Exclusion criteria include bleeding disorders, hypertension, inflammatory disorders, active gastrointestinal diseases, chronic use of low dose aspirin, consumption of restaurant or takeaway evening meals more than twice per week, use of dietary supplements rich in n-3 or n-6 fatty acids, habitual consumption of more than 1 fish meal per month, and plasma phospholipid EPA+DHA levels>7.9% of total fatty acids. Subjects are randomly allocated to one of three groups, designated ALA, SDA, and EPA.

A. Study Design

Following a 3-week run-in period, subjects ingest either ALA, SDA, EPA supplied as ethyl esters in capsules. Intakes are approximately 0.75 g/day for 3 weeks followed by 1.5 g/day for the subsequent 3 weeks. At each visit, blood is taken by venepuncture after an overnight fast. Blood is aliquoted into various tubes for the following procedures.

B. Cell Separations and Fatty Acid Analysis

Blood (e.g., 20 mL) is added to tubes containing EDTA in water and dextran in normal saline, pH 7.0. Erythrocytes are allowed to sediment under gravity at 37° C. for 30 min. The leucocyte-rich plasma is layered onto LYMPHOPREP, density 1.077 (Nycomed Pharma, Oslo) and centrifuged at 110 g for 10 min to separate leucocytes from the platelets, which are removed. The gradient is further centrifuged to separate the neutrophils from mononuclear cells, which are removed.

Samples are processed for fatty acid analysis as described in Mantzioris et al., *Am. J. Clin. Nutr.*, 72:42–8 (2000). Plasma, washed platelet and mononuclear cell pellets are stored frozen. Erythrocyte pellets are treated fresh with chloroform:isopropanol (2:1) and the lipid extracts stored at 4° C. Plasma, platelet and mononuclear cell pellets are extracted with chloroform:methanol. The cellular and plasma lipid extracts are fractionated by thin-layer chromatography. For the cellular extracts, the phospholipid fraction is retained and for the plasma extracts, the phospholipid, cholesterol ester, and triglyceride fractions are retained. These are transesterified by methanolysis (1% $H_2SO_4$ in methanol at 70° C. for 3 h). Fatty acid methyl esters are separated and quantified with a HEWLETT-PACKARD 6890 gas chromatograph equipped with a 50 m capillary column coated with BPX-70 (0.25 μm film thickness; SGE Pty Ltd, Victoria, Australia) (see Mantzioris et al., supra). Fatty acid standards are obtained (e.g., from NuChek Prep Inc., Elysian, Minn.) and include stearidonic acid obtained from Sigma Aldrich Pty Ltd. (Castle Hill, NSW, Australia). Organic solvents contain butylated hydroxy anisole (0.005%) as an antioxidant.

C. C-Reactive Protein and Plasma Lipids Analysis

C-reactive protein (Hs-CRP) in plasma can be analyzed by use of latex-enhanced immunonephelometric assay on a BN II analyzer (Rifai et al. Clinical efficacy of an automated high-sensitivity C-reactive protein assay. *Clin. Chem* 199; 45:2136). Or, blood is added to heparinised tubes, bacterial lipopolysaccharide (LPS) is added and the mixture incubated at 37° C., 5% $CO_2$, for 24 h. Plasma is collected and assayed for C-reactive protein by ELISA, using the procedures as described in Mantzioris et al, supra.

Blood (4 mL) is collected in heparinised tubes, and plasma total cholesterol, LDL and HDL cholesterol, and plasma triglycerides are measured.

D. Diet

Subjects are instructed to avoid dietary n-6 fatty acids and substituting monounsaturated (n-9) fatty acids where possible. To facilitate this pattern of intake, subjects are provided with foodstuffs low in n-6 fatty acids and high in monounsaturated (n-9) fatty acids. Subjects are provided with diet diaries and instructed in making weighed food records on designated days (weekdays and weekend days).

Diet diaries are analyzed to provide macronutrient (carbohydrate, protein, fat, alcohol, P:S ratio) intake data. This analysis also provides intake data on omega-6 and omega 9 fatty acids.

E. Statistical Analysis

For comparisons between visits within each group, repeated measures (ANOVA) followed by Newman-Keuls multiple comparisons test are used (e.g, Kwikstat, TexaSoft, Cedar Hill, Tex.). For comparisons between groups at each visit, ANOVA followed by Newman-Keuls multiple comparisons test is used (Kwikstat).

F. Analysis of Results

Subjects are weighed at each visit for change in weight during the trial. Returned capsule count is used to assess compliance for capsule intake. Fatty acids are analyzed between dietary groups in EPA concentration in erythrocyte or plasma phospholipids. The effect of ingestion of EPA, ALA or SDA at 0.75 g/day (weeks 0 to 3) or 1.5 g/day (weeks 3 to 6) is determined with respect to EPA concentration in the phospholipid fractions of erythrocytes and plasma. Effects on DPA concentration in the phospholipid fractions of erythrocytes and plasma are also analyzed. The correlation between SDA intake and C-reactive protein is analyzed, showing that administration of SDA results in a decrease in C-reactive protein.

In light of the detailed description of the invention and the examples presented above, it can be appreciated that the several aspects of the invention are achieved.

What is claimed is:

1. A method of increasing eicosapentaenoic acid (20:5, n-3) levels in a human, the method comprising:
   (a) identifying a human subject in need of increased eicosapentaenoic acid levels, wherein identifying the human subject comprises screening for an elevated presence of TNF-α and/or IL-1β; and
   (b) administering an effective amount of stearidonic acid (18:4, n-3) to the subject over a time period effective to increase eicosapentaenoic acid levels in the subject, wherein the subject metabolizes the stearidonic acid to eicosapentaenoic acid, resulting in increased eicosapentaenoic acid levels.

2. The method of claim 1, wherein the increased eicosapentaenoic acid (20:5, n-3) levels are present in tissues selected from the group consisting of erythrocyte phospholipids, platelet phospholipids, mononuclear cell phospholipids, plasma phospholipids, triglycerides, and cholesterol esters.

3. The method of claim 1, wherein the increased eicosapentaenoic acid levels down-regulate TNF-α and/or IL-1β.

4. The method of claim 1, wherein the effective amount of steeridonic acid administered is from about 0.1 g/day to about 10 g/day.

5. The method of claim 1, wherein the effective amount of stearidonic acid administered is from about 0.25 g/day to about 8 g/day.

6. The method of claim 1, wherein the effective amount of stearidonic acid administered is from about 0.5 gfday to about 5 g/day.

7. The method of claim 1 wherein the effective amount of stearidonic acid administered is about 1.5 g/day.

8. The method of claim 1, wherein identifying the human subject comprises screening for an elevated presence of TNF-α.

9. The method of claim 1, wherein identifying the human subject comprises screening for an elevated presence of IL-1β.

10. The method of claim 1, wherein identifying the human subject comprises screening for an elevated presence of TNF-α and IL-1β.

* * * * *

UNITED STATES PATENT AND TRADEMARK OFFICE
CERTIFICATE OF CORRECTION

PATENT NO. : 7,163,960 B2  Page 1 of 1
APPLICATION NO. : 10/384369
DATED : January 16, 2007
INVENTOR(S) : Ursin et al.

It is certified that error appears in the above-identified patent and that said Letters Patent is hereby corrected as shown below:

In claim 4, column 24, line 38, delete "steeridonic" and insert --stearidonic-- therefor.

In claim 6, column 24, line 45, delete "gfday" and insert --g/day-- therefor.

Signed and Sealed this

Twenty-ninth Day of May, 2007

JON W. DUDAS
*Director of the United States Patent and Trademark Office*